United States Patent [19]

Oyama et al.

[11] Patent Number: 5,214,177
[45] Date of Patent: May 25, 1993

[54] FLUORINATED ORGANIC SILICON COMPOUNDS AND METHOD FOR MAKING

[75] Inventors: Masayuki Oyama, Gunma; Toshio Takago, Annaka; Hideki Fujii, Annaka; Hitoshi Kinami, Annaka, all of Japan

[73] Assignee: Shin-Etsu Chemical Co., Ltd., Tokyo, Japan

[21] Appl. No.: 769,483

[22] Filed: Oct. 1, 1991

Related U.S. Application Data

[63] Continuation of Ser. No. 569,656, Aug. 20, 1990, abandoned.

[30] Foreign Application Priority Data

Aug. 21, 1989 [JP] Japan .................. 1-214663

[51] Int. Cl.$^5$ .................. C07F 7/08
[52] U.S. Cl. ....................... 556/448
[58] Field of Search ................ 556/448

[56] References Cited

U.S. PATENT DOCUMENTS

| | | | |
|---|---|---|---|
| 3,012,006 | 12/1961 | Holbrook et al. | 556/448 X |
| 3,331,813 | 7/1967 | Pittman et al. | 556/448 X |
| 3,422,131 | 1/1969 | Pittman et al. | 556/448 |
| 3,441,431 | 4/1969 | Pittman et al. | 117/121 |
| 4,898,958 | 2/1990 | Kishita et al. | 556/448 |
| 4,968,828 | 11/1990 | Yamamoto | 556/448 |

FOREIGN PATENT DOCUMENTS

| | | |
|---|---|---|
| 3830572A1 | 3/1989 | Fed. Rep. of Germany . |
| 1510788 | 1/1968 | France . |
| 0255288 | 10/1988 | Japan .................. 556/448 |

Primary Examiner—Paul F. Shaver
Attorney, Agent, or Firm—Birch, Stewart, Kolasch & Birch

[57] ABSTRACT

Fluorinated organic silicon compound of the general formula:

$$F-(CFCF_2O)_n-CF-CH_2CH_2-Si-R_{3-m} \quad (I)$$
$$\phantom{F-(}| \phantom{CF_2O)_n-}| \phantom{CH_2CH_2-}|$$
$$\phantom{F-(}CF_3 \phantom{F_2O)_n-}CF_3 \phantom{2CH_2-}Cl_m$$

wherein R is an alkyl group having 1 to 6 carbon atoms, n is an integer of from 1 to 6, and m is equal to 1, 2 or 3 are novel and useful as treating agents and intermediates for the synthesis of fluorinated cyclic organic silicon compounds. The fluorinated organic silicon compounds are prepared by reacting a chlorosilane with a fluorinated olefin.

7 Claims, 2 Drawing Sheets

FLUORINATED ORGANIC SILICON COMPOUNDS AND METHOD FOR MAKING

This application is a continuation of application Ser. No. 07/569,656 filed on Aug. 20, 1990, now abandoned.

BACKGROUND OF THE INVENTION

1. Field of the Invention

This invention relates to novel fluorinated organic silicon compounds and a method for preparing the same. The fluorinated organic silicon compounds are useful not only as surface treating agents, but also as intermediates for the synthesis of fluorinated cyclic organic silicon compounds.

2. Description of the Prior Art

A variety of silicone fluids and elastomers are known in the prior art and have been utilized in numerous applications. There still remains a need for organic silicon compounds from which siloxane polymers having heat resistance, chemical resistance, water and oil repellency, and mold releasability can be readily produced.

SUMMARY OF THE INVENTION

The inventors have found that a novel fluorinated organic silicon compound of the general formula:

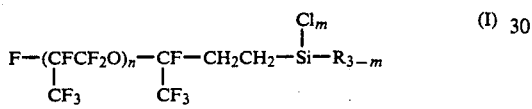

wherein R is an alkyl group having 1 to 6 carbon atoms, n is an integer of from 1 to 6, and m is equal to 1, 2 or 3 is produced by reacting a chlorosilane of the general formula:

wherein R and m are as defined above, with a fluorinated olefin of the general formula:

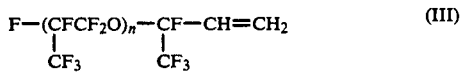

wherein n is as defined above in the presence of a catalyst.

The compounds of formula (I) possess both the reactivity of a chlorosilane and the attributes of fluorocarbon. Moreover, the extent to which the fluorocarbon attributes are exhibited can be controlled by changing the size of a fluorinated substituent. In this way, the compounds of formula (I) can be tailor for a particular purpose or application. Coupling of the silicon-containing substituent and the fluorinated substituent through a vinyl bond is chemically more stable than through an allyl bond. Therefore, the compounds of formula (I) are effective as silica treating agents for ≡Si—OH groups on silica surface which are blended in organic resins, silicone oil compounds and silicone rubbers, adhesion modifiers for resists used in the manufacture of semiconductor devices, and surface treating agents for imparting water and oil repellency and stain resistance to the surface of various glass articles including optical lenses, eyeglass lenses and glass instruments.

We have further found that by reacting a fluorinated dichlorosilane of the formula:

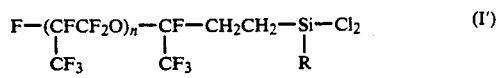

which corresponds to formula (I) wherein m is equal to 2, with a disiloxane diol of the general formula:

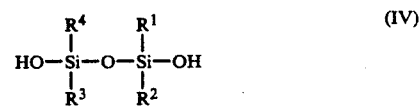

wherein $R^1$, $R^2$, $R^3$, and $R^4$ are independently selected from alkyl groups having 1 to 6 carbon atoms in the presence of a catalyst, there is produced a novel fluorinated cyclic organic silicon compound of the general formula:

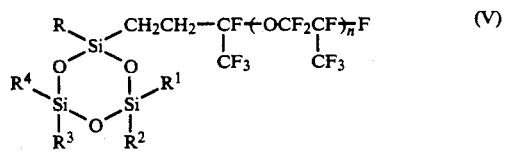

wherein R, n, and $R^1$ to $R^4$ are as defined above. This fluorinated cyclic organic silicon compound readily undergoes ring-opening polymerization in the presence of an alkali or acid catalyst to produce a chain siloxane polymer which has excellent heat resistance, chemical resistance, water and oil repellency, and mold releasability and is thus a useful starting material for silicone fluids and elastomers. Therefore, the compounds of formula (I) are also useful intermediates for the synthesis of the cyclic compounds of formula (V).

Briefly stated, the invention provides a fluorinated organic silicon compound of formula (I) as defined above and a method for preparing the compound of formula (I) by reacting a chlorosilane of formula (II) with a fluorinated olefin of formula (III) both as defined above.

DETAILED DESCRIPTION OF THE INVENTION

Figure 1:
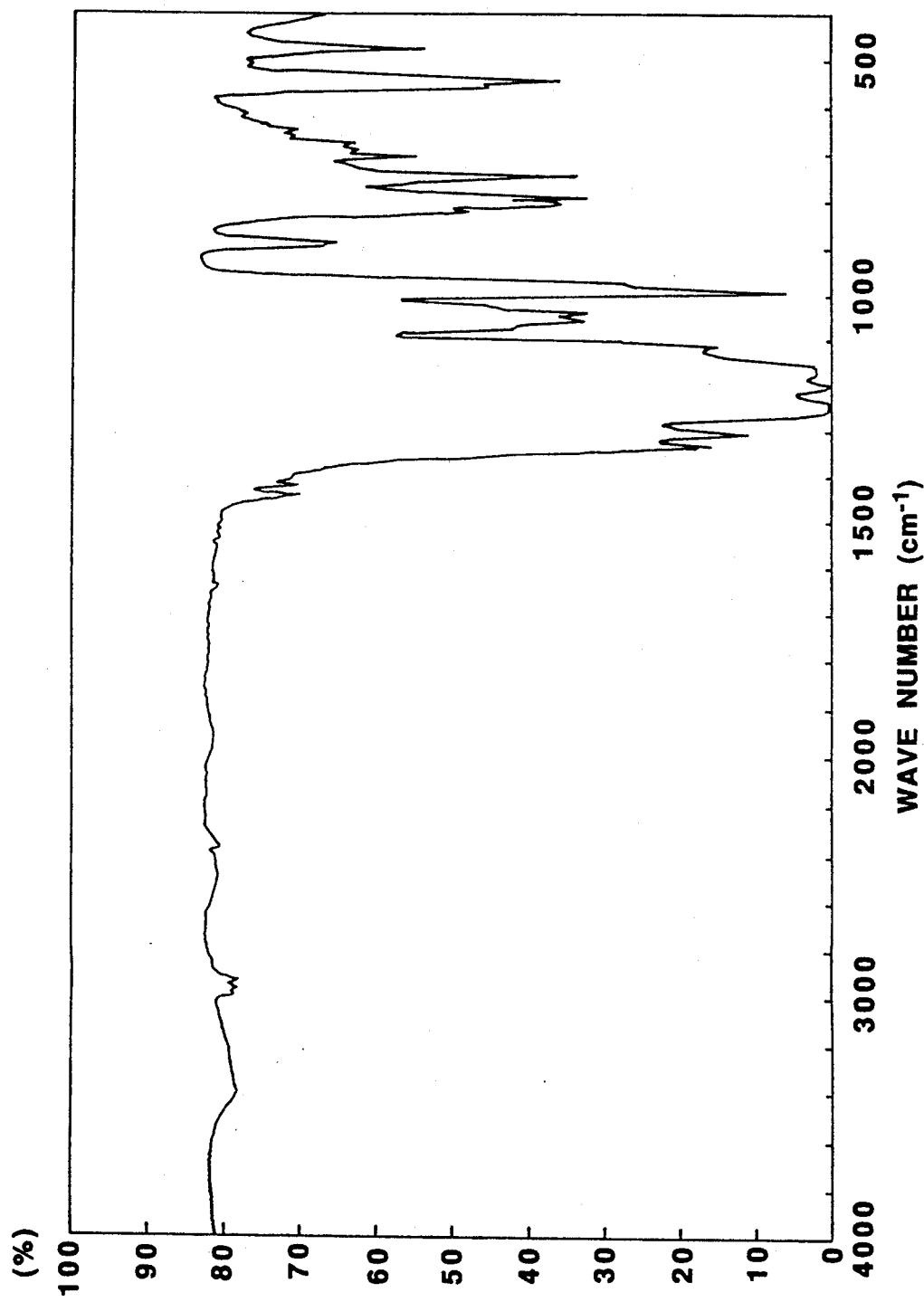
FIGS. 1 and 2 are charts showing infrared spectra of the end compounds obtained in Examples 1 and 2, respectively.

The fluorinated organic silicon compounds of the present invention are of the following general formula (I).

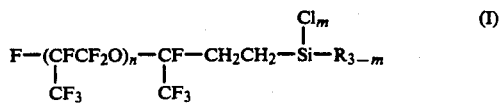

In the formula, R is an alkyl group having 1 to 6 carbon atoms, for example, such as methyl, ethyl, propyl, isopropyl and butyl groups, n is an integer of from 1 to 6, and m is equal to 1, 2 or 3.

The fluorinated organic silicon compounds of formula (I) can be readily synthesized, for example, by the following method.

The fluorinated organic silicon compounds of formula (I) can be produced by reacting a chlorosilane of the general formula:

$$H-\underset{\underset{R_{3-m}}{|}}{\overset{\overset{Cl_m}{|}}{Si}} \qquad (II)$$

wherein R and m are as defined above with a fluorinated olefin of the general formula:

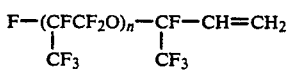

$$F-(CFCF_2O)_n-CF-CH=CH_2 \qquad (III)$$
with CF$_3$ groups on the indicated carbons wherein n is as defined above, typically in the presence of a platinum catalyst. Preferably, the chlorosilane and the fluorinated olefin are used in such amounts that 1 to 2 mol, more preferably 1.1 to 1.3 mol of the chlorosilane is present per mol of the fluorinated olefin. The platinum catalyst is used in a catalytic amount which preferably ranges from $1 \times 10^{-6}$ to $1 \times 10^{-3}$ mol, especially $1 \times 10^{-5}$ to $1 \times 10^{-4}$ mol of platinum per mol of the fluorinated olefin. The typical platinum catalysts used herein are platinum group metal catalysts, for example, chloroplatinic acid, alcohol modified chloroplatinic acids as disclosed in U.S. Pat. No. 3,220,972, chloroplatinic acid-olefin complexes as disclosed in U.S. Pat. Nos. 3,159,601, 3,159,662 and 3,775,452, platinum black and palladium on alumina, silica and carbon supports, and rhodium-olefin complexes. The reaction conditions may be suitably adjusted although preferred conditions include a reacting temperature of 50° to 150° C., expecially 70° to 110° C. and a reaction time of about 1 to about 100 hours, especially about 5 to about 20 hours.

The fluorinated olefin of formula (III) may e synthesized by the following per se known scheme.

(1) Oligomerization

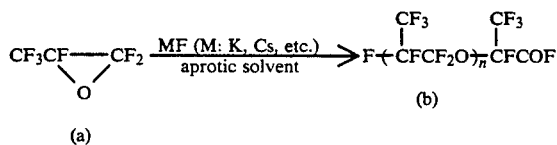

(a) → (b)

(2) Esterification

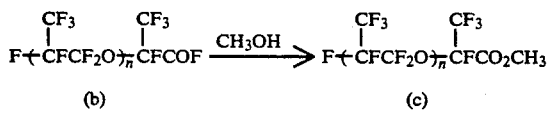

(b) → (c) via CH$_3$OH (3) Carbinol formation

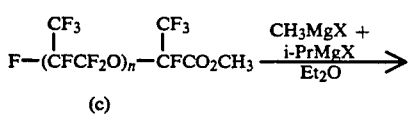

(c) → with CH$_3$MgX + i-PrMgX / Et$_2$O

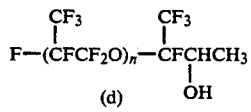

(d)

(4) Dehydration $$\underset{\underset{CF_3}{|}}{F-(CFCF_2O)_n}-\underset{\underset{OH}{|}}{\overset{\overset{CF_3}{|}}{CF}}-CHCH_3 \xrightarrow[(-H_2O)]{P_2O_5}$$

(d)

$$F-(CFCF_2O)_n-CFCH=CH_2$$
with CF$_3$ substituents (III)

In oligomerization step (1), by blowing hexafluoropropenoxide (HFPO) of formula (a) in an aprotic solvent system containing a metal fluoride such as potassium fluoride (KF), cesium fluoride (CsF) or the like at low temperatures of from −10° C. to 80° C., there is obtained an HFPO oligomeric acid fluoride of formula (b). The aprotic solvents used herein include diglyme, tetraglyme, aceto. nitrile, and dioxane.

Esterification reaction (2) is instantaneously completed by adding dropwise the separated oligomeric acid fluoride to excess methanol with cooling at 0° C. to 30° C. Purification and isolation is done by pouring the reaction mixture into an excessively large volume of water followed by decantation, neutralization, water washing and distillation. Alternatively, each of the ester oligomers of formula (c) may be isolated by fractionation after the HFPO oligomeric acid fluoride is poured into excess alcohol for esterification.

Carbinol formation (3) may be effected by dissolving the ester of formula (c) in a solvent such as ethyl ether, adding a Grignard reagent in the form of a mixture of methyl and isopropyl magnesium halides, and heating the reaction mixture. For example, an ether solution of the ester is added dropwise to a Grignard reagent at 0° to 5° C. and the reaction mixture is then stirred for one day at room temperature. The isopropyl Grignard reagent acts as a reducing agent.

Dehydration (4) is effected at a temperature of 300° to 400° C. in the presence of phosphorus pentoxide, resulting in a fluorinated olefin of formula (III).

The novel fluorinated organic silicon compounds of formula (I) according to the invention possess both the reactivity of chlorosilane and the attribute of fluorocarbon in such a manner that the attribute of fluorocarbon may be controlled for a particular purpose or application by changing the size of a fluorinated substituent. Therefore, these compounds are effective as silica treating agents for Si-OH groups on silica surface which are blended in organic resins, silicone oil compounds and silicone rubbers, adhesion modifiers for resists used in the manufacture of semiconductor devices, and surface treating agents for imparting water and oil repellency and stain resistance to the surface of various glass articles including optical lenses, eyeglass lenses and glass instruments.

Further, by reacting a difunctional fluorinated organic silicon compound or dichlorosilane of the formula:

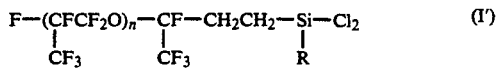

$$F-(CFCF_2O)_n-CF-CH_2CH_2-Si-Cl_2 \qquad (I')$$
with CF$_3$, CF$_3$, R substituents which corresponds to formula (I) wherein m is equal to 2, with a disiloxane diol of the general formula:

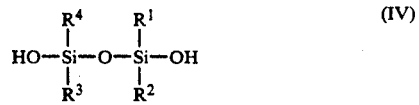

wherein $R^1$, $R^2$, $R^3$, and $R^4$, which may be the same or different, are independently selected from alkyl groups having 1 to 6 carbon atoms in the presence of a catalyst, there is produced a novel fluorinated cyclic organic silicon compound of the general formula:

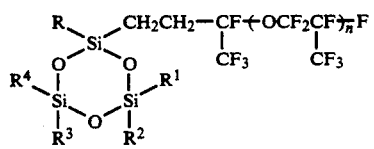

wherein R, n, and $R^1$ to $R^4$ are as defined above. The molar ratio of (I') to (IV) preferably ranges from 2:1 to 1:2, more preferably from 1:1 to 1:1.3.

The catalysts used herein include amines such as triethylamine, pyridine, dimethylaniline, and diethylamine. They are preferably used in amounts of 1 to 6 mol, especially 2 to 3 mol per mol of the dichlorosilane. The reaction temperature preferably ranges from 0° to 100° C., especially 30° to 70° C.

The reaction may be carried out by separately preparing solutions of the compounds of formulae (I') and (IV) and adding them to a solution containing the catalyst. The preferred solvent for the disiloxane diol of formula (IV) is a polar solvent such as methyl ethyl ketone, acetone, and ethyl acetate whereas the solvent for the dichlorosilane having a fluorinated substituent of formula (I') is a fluorinated solvent such as xylene hexafluoride, perfluoro. octane, and 1,1,2-trichlorotrifluoroethane.

The novel organic silicon compounds of formula (V) are useful starting materials for preparing silicone fluids and elastomers. For instance, they are likely to undergo ring-opening polymerization in the presence of an alkali catalyst such as KOH and (n $C_4H_9)_4$POH or acid catalyst such as $H_2SO_4$ and $CF_3SO_3H$ by way of equilibration reaction as known for the conventional hexamethylcyclotrisiloxane, to thereby produce chain siloxane polymers. These chain siloxane polymers are useful starting materials for preparing silicone fluids and elastomers. Since the organic silicon compounds have a substituent containing many fluorine atoms in their molecule, they polymerize into siloxane polymers which not only have improved heat resistance, chemical resistance and weatherability, but also exhibit higher water and oil repellency and mold releasability than conventional ones because of reduced polymer surface energy.

There have been described novel fluorinated organic silicon compound of formula (I) which can find a wide variety of applications as such and at the same time, are useful intermediates for the synthesis of novel fluorinated cyclic organic silicon compounds of formula (V).

EXAMPLE

Examples of the present invention are given below by way of illustration and not by way of limitation. Unless otherwise stated, percents are by weight.

EXAMPLE 1

A 350-ml autoclave was charged with 105 grams of dichloromethylsilane and 36 grams of a fluorinated olefin of the following formula (IIIa) and further with 0.05 grams of a platinum catalyst.

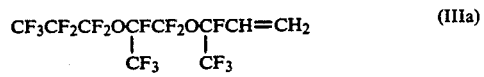

The autoclave was then heated to 120° C. and kept at the temperature for 50 hours for reaction. The reaction mixture was distilled, obtaining 76 grams (yield 60%) of a fraction having a boiling point of 76° C./8 mmHg.

The fraction was identified to be an organic silicon compound of the following formula:

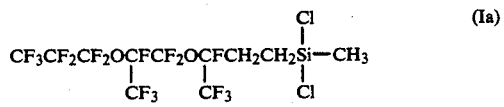

through measurement of infrared (IR) absorption spectrum and nuclear magnetic resonance (NMR) spectrum as reported below.

IR spectrum: see FIG. 1.
950 cm$^{-1}$ (C—H)
1100–1340 cm$^{-1}$ (C—F)
$^1$H-NMR spectrum:
(solvent: CCl$_4$, internal standard: CHCl$_3$)
0.9 (s, 3H, Si—CH$_3$)
1.1–1.6 (m, 2H, Si—CH$_2$—C)
2.1–2.7 (m, 2H, Si—C—CH$_2$—C)

EXAMPLE 2

A 350-ml autoclave was charged with 36.0 grams of trichlorosilane and 67.0 grams of a fluorinated olefin of the following formula (IIIb) and further with 0.11 grams of a platinum catalyst.

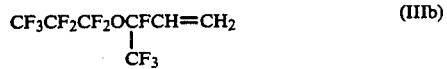

The autoclave was then heated to 120° C. and kept at the temperature for 17½ hours for reaction. The reaction mixture was worked up and distilled, obtaining 58 grams (yield 59%) of a fraction having a boiling point of 83° C./50

The fraction was identified to be an organic silicon compound of the following formula:

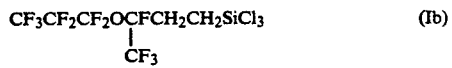

through measurement of IR and NMR spectra as reported below.

Figure 2:
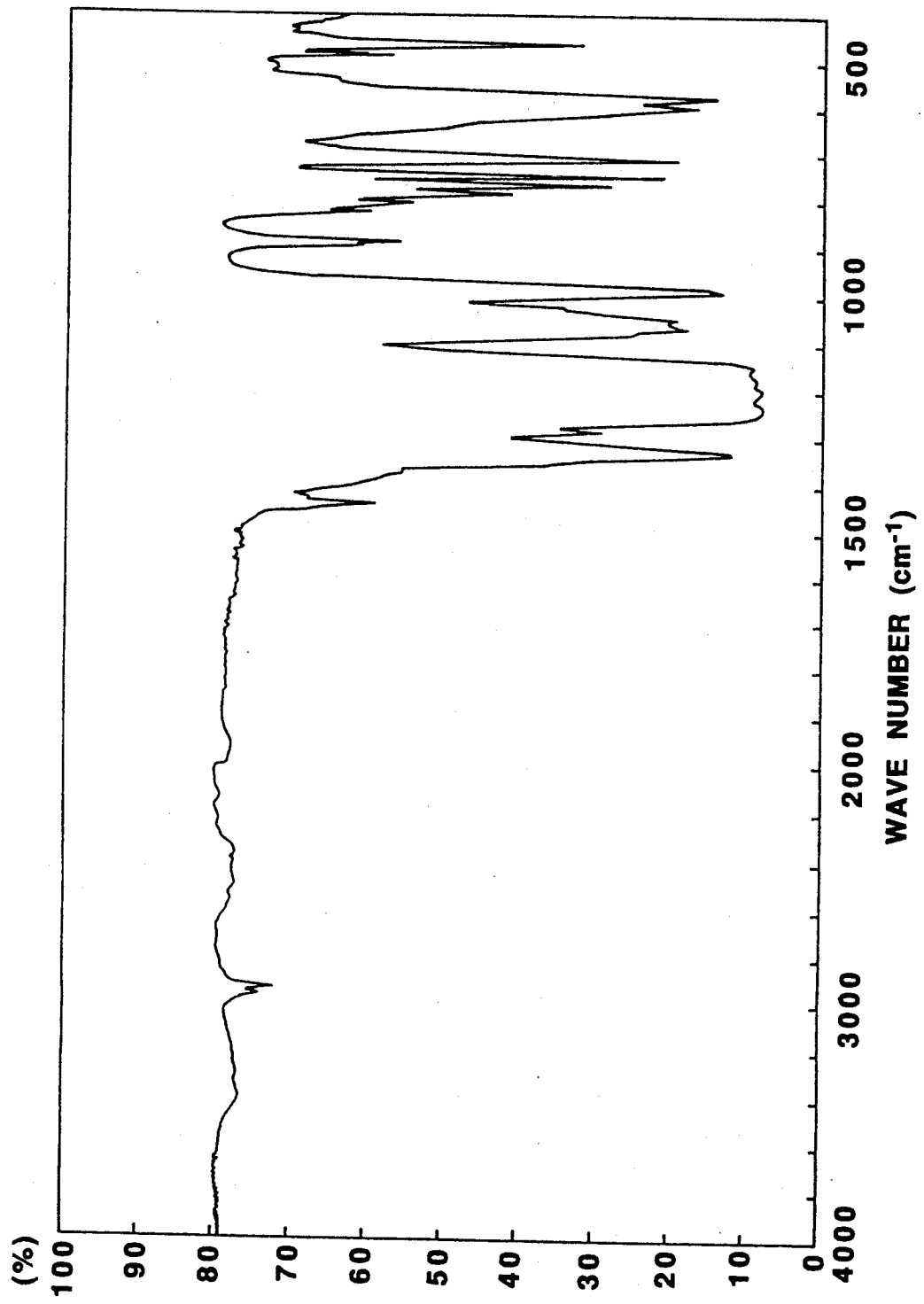

IR spectrum: see FIG. 2.
2950 cm$^{-1}$ (C—H)
100–1340 cm$^{-1}$ (C—F)
$^1$H-NMR spectrum:
(solvent: CCl$_4$, internal standard: CHCl$_3$)
2.1–2.9 (m, 2H, Si—C—CH$_2$—C)

REFERENCE EXAMPLE

A four-necked flask having an interior volume of 2 liters was charged with 600 ml of metaxylene hexafluoride in which 44 grams of triethylamine was dissolved. The flask was equipped with two dropping funnels each having an interior volume of 500 ml. One funnel was charged with 198 grams of a fluorinated dichlorosilane of formula (Ia) obtained in Example 1 in 150 ml of metaxylene hexafluoride whereas the other funnel charged with 55 grams of a disiloxane diol of the formula:

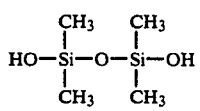

(IVa)

in 150 ml of methyl ethyl ketone. After the triethylamine solution in the flask was heated to 50©C, the dichlorosilane and disiloxane dirol solutions were added dropwise from the respective funnels at an approximately equal rate of about 1 ml/min. After dropwise addition, the reaction mixture was stirred for 30 minutes to complete reaction. The reaction product was washed with water to remove the triethylamine hydrochloride by-product and the separated organic layer was distilled in vacuum, obtaining 188 grams (yield 82%) of a fraction having a boiling point of 77° C./2 mmHg.

The compound was subjected to elemental analysis and measured for IR and NMR spectra, with the following results.

Elemental analysis: $C_{15}H_{19}O_5F_{17}Si_3$

|  | C | H | Si | F |
|---|---|---|---|---|
| Calcd. (%) | 26.24 | 2.77 | 12.24 | 47.08 |
| Found (%) | 26.27 | 2.81 | 12.21 | 47.11 |

IR spectrum: specific absorption
1020 cm$^{-1}$ (Si—O)
1000–1400 cm$^{-1}$ (C—F)
NMR spectrum: δ (ppm)
(solvent: Fron 113, internal standard: CHCl$_3$)
0.40–0.88 (m, 2H, Si—CH$_2$—C)
1.72–2.45 (m, 2H, CF—CH$_2$—C)

Based on these results, the compound was identified to be a fluorinated cyclic organic silicon compound of the following formula.

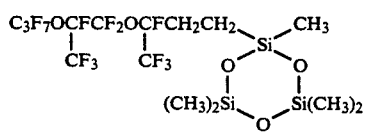

(Va)

Although some preferred embodiments have been described, many modifications and variations may be made thereto in the light of the above teachings.

Such variations are not to be regarded as a departure from the spirit and scope of the invention, and all such modifications as would be obvious to one skilled in the art are intended to be included within the scope of the following claims.

We claim:

1. A fluorinated organic silicon compound of the general formula:

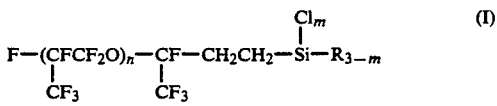

(I)

wherein R is an alkyl group having 1 to 6 carbon atoms, n is an integer of from 1 to 6, m is equal to 1, 2 or 3.

2. The fluorinated organic silicon compound of claim 1, wherein r is an alkyl group selected from the group consisting of methyl, ethyl, propyl, isopropyl, and butyl.

3. The fluorinated organic silicon compound of claim 2, wherein R is methyl.

4. The fluorinated organic silicon compound of claim 1, wherein m is 2.

5. The fluorinated organic silicon compound of claim 1, wherein n is 2.

6. The fluorinated organic silicon compound of claim 1, wherein R is methyl, m is 2, and n is 2.

7. The fluorinated organic silicon compound of claim 1, wherein said compound is produced by a method which comprises reacting a chlorosilane of the general formula (II):

(II)

wherein R and m are as defined in claim 1, with a fluorinated olefin of the general formula (III):

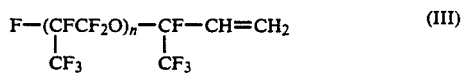

(III)

wherein n is as defined in claim 1, in the presence of a platinum group metal catalyst; and wherein said fluorinated olefin of the general formula III is prepared by a method which comprises:

(1) subjecting hexafluoropropyloxide to oligomerization in the presence of an aprotic solvent and a metal fluoride;
(2) verifying the oligomer product of step (1) by reacting said oligomer project of step (1) with methanol;
(3) subjecting the ester product of the step (2) to carbinol formation by combining said ester product with methyl magnesium halide and isopropyl magnesium halide; and
(4) dehydrating the reaction product of step (3) in the presence of phosphorus pentoxide to thereby form said fluorinated olefin of general formula (III).

* * * * *